US012226647B2

(12) United States Patent
Kubota et al.

(10) Patent No.: US 12,226,647 B2
(45) Date of Patent: Feb. 18, 2025

(54) METHOD AND APPARATUS FOR TREATING REFRACTIVE ERROR OF THE EYE

(71) Applicant: ACUCELA INC., Seattle, WA (US)

(72) Inventors: Ryo Kubota, Seattle, WA (US); Amitava Gupta, Roanoke, VA (US)

(73) Assignee: ACUCELA INC., Seattle, WA (US)

( * ) Notice: Subject to any disclaimer, the term of this patent is extended or adjusted under 35 U.S.C. 154(b) by 0 days.

(21) Appl. No.: 17/052,906

(22) PCT Filed: May 3, 2019

(86) PCT No.: PCT/US2019/030682
§ 371 (c)(1),
(2) Date: Nov. 4, 2020

(87) PCT Pub. No.: WO2019/217241
PCT Pub. Date: Nov. 14, 2019

(65) Prior Publication Data
US 2021/0069524 A1    Mar. 11, 2021

Related U.S. Application Data

(60) Provisional application No. 62/669,580, filed on May 10, 2018.

(51) Int. Cl.
*A61N 5/06* (2006.01)
*A61N 5/067* (2006.01)
*G02C 7/04* (2006.01)

(52) U.S. Cl.
CPC ............ *A61N 5/0613* (2013.01); *G02C 7/04* (2013.01); *A61N 2005/0632* (2013.01);
(Continued)

(58) Field of Classification Search
CPC ................. A61N 5/0613; A61N 5/067; A61N 2005/0632; A61N 2005/0648;
(Continued)

(56) References Cited

U.S. PATENT DOCUMENTS 2,350,386 A    6/1944    Christman
6,516,808 B2   2/2003    Schulman
(Continued)

FOREIGN PATENT DOCUMENTS

CN    215494397      1/2022
EP    3153139 A1     4/2017
(Continued)

OTHER PUBLICATIONS

International Search Report and Written Opinion for International Application No. PCT/US2019/030682, 8 pages (Jul. 17, 2019).
(Continued)

*Primary Examiner* — Yingchuan Zhang
*Assistant Examiner* — Sebastian X Lukjan
(74) *Attorney, Agent, or Firm* — FisherBroyles, LLP; John K. Shimmick

(57) ABSTRACT

A source of light energy such as a source of violet light energy is coupled to a structure configured to contact the eye. The light source and structure are arranged to provide therapeutic amounts of violet light energy to the eye in order to inhibit the progression of refractive error such as myopia. The light source can be configured in many ways and may comprise a radioisotope and a phosphorescent material. The structure configured to contact the eye may comprise a contact lens or an implant.

15 Claims, 1 Drawing Sheet

(52) U.S. Cl.
CPC ............... *A61N 2005/0648* (2013.01); *A61N 2005/0651* (2013.01); *A61N 2005/0663* (2013.01); *A61N 5/067* (2021.08); *G02C 2202/24* (2013.01)

(58) Field of Classification Search
CPC .... A61N 2005/0651; A61N 2005/0663; A61N 5/1029; A61N 2005/0662; A61N 2005/0661; G02C 7/04; G02C 2202/24; A61F 9/0079
See application file for complete search history.

(56) References Cited

U.S. PATENT DOCUMENTS

| | | | |
|---|---|---|---|
| 7,018,040 B2 | 3/2006 | Blum | |
| 8,057,034 B2 | 11/2011 | Ho | |
| 8,246,167 B2 | 8/2012 | Legerton | |
| 8,432,124 B2 | 4/2013 | Foster | |
| 8,662,664 B2 | 3/2014 | Artal Soriano | |
| 8,857,983 B2 | 10/2014 | Pugh | |
| 8,960,899 B2 | 2/2015 | Etzkorn | |
| 9,054,079 B2 | 6/2015 | Etzkorn | |
| 9,176,332 B1 | 11/2015 | Etzkorn | |
| 9,345,813 B2 | 5/2016 | Hogg | |
| 9,482,882 B1 | 11/2016 | Hanover | |
| 9,482,883 B1 | 11/2016 | Meisenholder | |
| 9,726,904 B1 | 8/2017 | Lin | |
| 9,763,827 B2 | 9/2017 | Kelleher | |
| 9,885,884 B2 | 2/2018 | Drobe | |
| 9,889,615 B2 | 2/2018 | Pugh | |
| 9,918,894 B2 | 3/2018 | Lam | |
| 9,962,071 B2 | 5/2018 | Yates | |
| 10,133,092 B2 | 11/2018 | Tsubota | |
| 10,139,521 B2 | 11/2018 | Tran | |
| 10,146,067 B2 | 12/2018 | Tsai | |
| 10,231,897 B2 | 3/2019 | Tse | |
| 10,268,050 B2 | 4/2019 | To | |
| 10,359,648 B2 | 7/2019 | Kim | |
| 10,591,745 B1 | 3/2020 | Lin | |
| 10,788,686 B2 | 9/2020 | Tsai | |
| 10,884,264 B2 | 1/2021 | Hones | |
| 10,921,612 B2 | 2/2021 | Zhou | |
| 10,993,515 B1 | 5/2021 | Kim | |
| 11,000,186 B2 | 5/2021 | Linder | |
| 11,187,921 B2 | 11/2021 | Zhou | |
| 11,219,287 B1 | 1/2022 | Kim | |
| 11,275,259 B2 | 3/2022 | Kubota | |
| 11,281,022 B2 | 3/2022 | Buscemi | |
| 11,320,674 B2 | 5/2022 | Kubota | |
| 11,358,001 B2 | 6/2022 | Kubota | |
| 11,366,339 B2 | 6/2022 | Kubota | |
| 11,366,341 B1 | 6/2022 | Kubota | |
| 11,388,968 B2 | 7/2022 | Dabov | |
| 11,395,959 B2 | 7/2022 | Stemple | |
| 11,402,662 B2 | 8/2022 | Wyss | |
| 11,409,136 B1 | 8/2022 | Kubota | |
| 11,415,818 B2 | 8/2022 | Olgun | |
| 11,444,488 B2 | 9/2022 | Bohn | |
| 11,446,514 B2 | 9/2022 | Bahmani | |
| 11,460,720 B1 | 10/2022 | Kubota | |
| 11,467,423 B2 | 10/2022 | Buscemi | |
| 11,467,426 B2 | 10/2022 | Kubota | |
| 11,467,428 B2 | 10/2022 | Kubota | |
| 11,470,936 B2 | 10/2022 | Kim | |
| 11,480,813 B2 | 10/2022 | Kubota | |
| 11,531,216 B2 | 12/2022 | Kubota | |
| 11,583,696 B2 | 2/2023 | Kubota | |
| 11,619,831 B2 | 4/2023 | Wyss | |
| 11,630,329 B2 | 4/2023 | Kubota | |
| 11,656,483 B2 | 5/2023 | Ice | |
| 11,681,162 B2 | 6/2023 | Zhou | |
| 11,681,164 B2 | 6/2023 | Jamshidi | |
| 11,693,259 B2 | 7/2023 | Buscemi | |
| 11,719,957 B2 | 8/2023 | Kubota | |
| 11,733,545 B2 | 8/2023 | Kubota | |
| 11,777,340 B2 | 10/2023 | Kubota | |
| 11,971,615 B2 | 4/2024 | Kubota | |
| 11,986,669 B2 | 5/2024 | Kubota | |
| 2002/0186345 A1* | 12/2002 | Duppstadt | G02C 7/044 351/159.05 |
| 2004/0237971 A1 | 12/2004 | Radhakrishnan | |
| 2005/0258053 A1 | 11/2005 | Sieg | |
| 2006/0082729 A1 | 4/2006 | To | |
| 2006/0227067 A1 | 10/2006 | Iwasaki | |
| 2007/0115431 A1 | 5/2007 | Smith, III | |
| 2007/0153231 A1 | 7/2007 | Iuliano | |
| 2007/0281752 A1 | 12/2007 | Lewis | |
| 2008/0231799 A1 | 9/2008 | Iuliano | |
| 2008/0231801 A1 | 9/2008 | Iuliano | |
| 2008/0291391 A1 | 11/2008 | Meyers | |
| 2008/0309882 A1 | 12/2008 | Thorn | |
| 2009/0187242 A1 | 7/2009 | Weeber | |
| 2009/0201460 A1 | 8/2009 | Blum | |
| 2009/0204207 A1 | 8/2009 | Blum | |
| 2010/0076417 A1 | 3/2010 | Suckewer | |
| 2010/0294675 A1 | 11/2010 | Mangano | |
| 2010/0296058 A1 | 11/2010 | Ho | |
| 2011/0085129 A1 | 4/2011 | Legerton | |
| 2011/0153012 A1 | 6/2011 | Legerton | |
| 2011/0202114 A1* | 8/2011 | Kessel | A61F 9/008 607/88 |
| 2012/0055817 A1 | 3/2012 | Newman | |
| 2012/0199995 A1 | 8/2012 | Pugh | |
| 2012/0206485 A1 | 8/2012 | Osterhout | |
| 2012/0212399 A1 | 8/2012 | Border | |
| 2012/0215291 A1* | 8/2012 | Pugh | G02C 7/04 607/93 |
| 2013/0027655 A1 | 1/2013 | Blum | |
| 2013/0072828 A1 | 3/2013 | Sweis | |
| 2013/0135578 A1 | 5/2013 | Pugh | |
| 2013/0194540 A1 | 8/2013 | Pugh | |
| 2013/0278887 A1 | 10/2013 | Legerton | |
| 2013/0317487 A1 | 11/2013 | Luttrull | |
| 2014/0039361 A1 | 2/2014 | Siu | |
| 2014/0085601 A1 | 3/2014 | Etzkorn | |
| 2014/0194773 A1 | 7/2014 | Pletcher | |
| 2014/0218647 A1 | 8/2014 | Blum | |
| 2014/0240665 A1 | 8/2014 | Pugh | |
| 2014/0268029 A1 | 9/2014 | Pugh | |
| 2014/0277291 A1 | 9/2014 | Pugh | |
| 2014/0306361 A1 | 10/2014 | Pugh | |
| 2014/0379054 A1 | 12/2014 | Cooper et al. | |
| 2015/0018599 A1 | 1/2015 | Legerton | |
| 2015/0057701 A1* | 2/2015 | Kelleher | A61H 23/0245 606/204.15 |
| 2015/0109574 A1 | 4/2015 | Tse | |
| 2015/0160477 A1 | 6/2015 | Dai | |
| 2015/0200554 A1 | 7/2015 | Marks | |
| 2015/0241706 A1 | 8/2015 | Schowengerdt | |
| 2016/0016004 A1 | 1/2016 | Hudson | |
| 2016/0056498 A1 | 2/2016 | Flitsch | |
| 2016/0067037 A1 | 3/2016 | Rosen | |
| 2016/0067087 A1* | 3/2016 | Tedford | A61N 5/0624 606/4 |
| 2016/0091737 A1 | 3/2016 | Kim | |
| 2016/0143801 A1 | 5/2016 | Yin | |
| 2016/0158486 A1 | 6/2016 | Colbaugh | |
| 2016/0270656 A1 | 9/2016 | Samec | |
| 2016/0299357 A1 | 10/2016 | Hayashi | |
| 2016/0377884 A1 | 12/2016 | Lau | |
| 2017/0000326 A1 | 1/2017 | Samec | |
| 2017/0001032 A1 | 1/2017 | Samec | |
| 2017/0010480 A1 | 1/2017 | Blum | |
| 2017/0014074 A1 | 1/2017 | Etzkorn | |
| 2017/0055823 A1 | 3/2017 | Lu | |
| 2017/0072218 A1 | 3/2017 | Rucker | |
| 2017/0115512 A1 | 4/2017 | Pugh | |
| 2017/0184875 A1 | 6/2017 | Newman | |
| 2017/0270636 A1 | 9/2017 | Shtukater | |
| 2017/0276963 A1 | 9/2017 | Brennan | |
| 2017/0307779 A1 | 10/2017 | Marullo | |
| 2017/0367879 A1* | 12/2017 | Lopath | A61F 9/009 |
| 2018/0017810 A1 | 1/2018 | Wu | |

(56) References Cited

U.S. PATENT DOCUMENTS

| | | | |
|---|---|---|---|
| 2018/0017814 A1* | 1/2018 | Tuan | A61H 5/005 |
| 2018/0052319 A1 | 2/2018 | Mccabe | |
| 2018/0055351 A1 | 3/2018 | Yates | |
| 2018/0074322 A1 | 3/2018 | Rousseau | |
| 2018/0090958 A1 | 3/2018 | Steger | |
| 2018/0092738 A1 | 4/2018 | Tai | |
| 2018/0136486 A1 | 5/2018 | Macnamara | |
| 2018/0136491 A1 | 5/2018 | Ashwood | |
| 2018/0161231 A1 | 6/2018 | Tse | |
| 2018/0173010 A1 | 6/2018 | Harant | |
| 2018/0188556 A1 | 7/2018 | Portney | |
| 2018/0221140 A1 | 8/2018 | Rosen | |
| 2018/0264284 A1 | 9/2018 | Alvarez | |
| 2018/0275427 A1 | 9/2018 | Lau | |
| 2018/0345034 A1 | 12/2018 | Butzloff | |
| 2019/0033618 A1 | 1/2019 | Choi | |
| 2019/0033619 A1 | 1/2019 | Neitz | |
| 2019/0049730 A1 | 2/2019 | Miller | |
| 2019/0076241 A1 | 3/2019 | Alarcon Heredia | |
| 2019/0092545 A1 | 3/2019 | Oag | |
| 2019/0129204 A1 | 5/2019 | Tsubota | |
| 2019/0227342 A1 | 7/2019 | Brennan | |
| 2019/0235279 A1 | 8/2019 | Hones | |
| 2019/0247675 A1 | 8/2019 | Legerton | |
| 2019/0250413 A1* | 8/2019 | Martin | H04N 23/63 |
| 2019/0250432 A1 | 8/2019 | Kim | |
| 2019/0314147 A1 | 10/2019 | Blum | |
| 2019/0318589 A1 | 10/2019 | Howell | |
| 2020/0026082 A1 | 1/2020 | Park | |
| 2020/0033637 A1 | 1/2020 | Jamshidi | |
| 2020/0073148 A1 | 3/2020 | Alhaideri | |
| 2020/0089023 A1 | 3/2020 | Zhou | |
| 2020/0108272 A1 | 4/2020 | Bahmani | |
| 2020/0110265 A1 | 4/2020 | Serdarevic | |
| 2020/0133024 A1 | 4/2020 | Paune Fabre | |
| 2020/0142219 A1 | 5/2020 | Rousseau | |
| 2020/0264455 A1 | 8/2020 | Olgun | |
| 2020/0364992 A1 | 11/2020 | Howell | |
| 2021/0018762 A1 | 1/2021 | Zheleznyak | |
| 2021/0031051 A1 | 2/2021 | Kubota | |
| 2021/0048690 A1 | 2/2021 | Guillot | |
| 2021/0231977 A1 | 7/2021 | Zhou | |
| 2021/0263336 A1 | 8/2021 | Gupta | |
| 2021/0298440 A1 | 9/2021 | Kim | |
| 2021/0329764 A1 | 10/2021 | Linder | |
| 2021/0356767 A1 | 11/2021 | Kubota | |
| 2021/0376661 A1 | 12/2021 | Bohn | |
| 2021/0379399 A1 | 12/2021 | Buscemi | |
| 2021/0382325 A1 | 12/2021 | Kubota | |
| 2021/0382326 A1 | 12/2021 | Kubota | |
| 2021/0389607 A1 | 12/2021 | Buscemi | |
| 2022/0057651 A1 | 2/2022 | Segre | |
| 2022/0107508 A1 | 4/2022 | Zhou | |
| 2022/0128842 A1 | 4/2022 | Ice | |
| 2022/0179213 A1 | 6/2022 | Zhou | |
| 2022/0197059 A1 | 6/2022 | Zhou | |
| 2022/0231523 A1 | 7/2022 | Bristol | |
| 2022/0257972 A1 | 8/2022 | Kubota | |
| 2022/0299795 A1 | 9/2022 | Wyss | |
| 2022/0390766 A1 | 12/2022 | Kubota | |
| 2022/0390768 A1 | 12/2022 | Kubota | |
| 2022/0397775 A1 | 12/2022 | Bahmani | |
| 2022/0404641 A1 | 12/2022 | Kubota | |
| 2022/0413318 A1 | 12/2022 | Kubota | |
| 2023/0026567 A1 | 1/2023 | Buscemi | |
| 2023/0089006 A1 | 3/2023 | Kubota | |
| 2023/0324717 A1 | 10/2023 | Kubota | |

FOREIGN PATENT DOCUMENTS

| | | |
|---|---|---|
| EP | 3232254 | 10/2017 |
| EP | 3255478 | 12/2017 |
| EP | 3413116 | 12/2018 |
| EP | 3640713 | 4/2020 |
| JP | 2006292883 | 10/2006 |
| JP | 2011518355 | 6/2011 |
| JP | 2014508585 | 4/2014 |
| JP | 2017173847 | 9/2017 |
| JP | 2017219847 | 12/2017 |
| KR | 20180038359 | 4/2018 |
| KR | 20180038359 A | 4/2018 |
| TW | M356929 | 5/2009 |
| TW | 201234072 | 8/2012 |
| TW | 201734580 | 10/2017 |
| WO | 2009074638 A2 | 6/2009 |
| WO | 2009074638 A3 | 6/2009 |
| WO | 2009121810 A1 | 10/2009 |
| WO | 2009129528 | 10/2009 |
| WO | 2010015255 A1 | 2/2010 |
| WO | 2010043599 A1 | 4/2010 |
| WO | 2011008846 | 1/2011 |
| WO | 2011089042 A1 | 7/2011 |
| WO | 2011153158 | 12/2011 |
| WO | 2011163559 | 12/2011 |
| WO | 2012018583 | 2/2012 |
| WO | 2012037019 | 3/2012 |
| WO | 2012106542 | 8/2012 |
| WO | 2012118777 | 9/2012 |
| WO | 2012129210 | 9/2012 |
| WO | 2012136470 A1 | 10/2012 |
| WO | 2012138426 | 10/2012 |
| WO | 2013059195 | 4/2013 |
| WO | 2013059656 | 4/2013 |
| WO | 2013059663 | 4/2013 |
| WO | 2013087518 A1 | 6/2013 |
| WO | 2013112748 | 8/2013 |
| WO | 2013112803 | 8/2013 |
| WO | 2013112862 | 8/2013 |
| WO | 2013112868 | 8/2013 |
| WO | 2013130803 | 9/2013 |
| WO | 2013151728 | 10/2013 |
| WO | 2014004836 | 1/2014 |
| WO | 2014004839 | 1/2014 |
| WO | 2014018104 | 1/2014 |
| WO | 2014033035 A1 | 3/2014 |
| WO | 2014050879 | 4/2014 |
| WO | 2014052012 | 4/2014 |
| WO | 2014117173 | 7/2014 |
| WO | 2014120928 | 8/2014 |
| WO | 2014161002 | 10/2014 |
| WO | 2014178221 | 11/2014 |
| WO | 2014191460 A1 | 12/2014 |
| WO | 2015063097 A1 | 5/2015 |
| WO | 2015095891 | 6/2015 |
| WO | 2015105881 | 7/2015 |
| WO | 2015164564 | 10/2015 |
| WO | 2015186723 | 12/2015 |
| WO | 2016019346 | 2/2016 |
| WO | 2016019351 | 2/2016 |
| WO | 2017039672 | 3/2017 |
| WO | 2017083770 | 5/2017 |
| WO | 2017083774 | 5/2017 |
| WO | 2017/094886 A1 | 6/2017 |
| WO | 2017168122 | 10/2017 |
| WO | 2018014712 | 1/2018 |
| WO | 2018014712 A1 | 1/2018 |
| WO | 2018014960 | 1/2018 |
| WO | 2018057804 | 3/2018 |
| WO | 2018075229 | 4/2018 |
| WO | 2018085576 | 5/2018 |
| WO | 2018088980 | 5/2018 |
| WO | 2018089699 | 5/2018 |
| WO | 2018208724 | 11/2018 |
| WO | 2019100941 | 5/2019 |
| WO | 2019114463 | 6/2019 |
| WO | 2019191510 | 10/2019 |
| WO | 2019217241 | 11/2019 |
| WO | 2020014074 | 1/2020 |
| WO | 2020014613 | 1/2020 |
| WO | 2020025355 | 2/2020 |
| WO | 2020028177 | 2/2020 |
| WO | 2020069232 | 4/2020 |
| WO | 2021056018 | 3/2021 |
| WO | 2021116449 | 6/2021 |

(56) References Cited

FOREIGN PATENT DOCUMENTS

| WO | 2021168481 | 8/2021 |
|---|---|---|
| WO | 2021231684 | 11/2021 |
| WO | 2021252318 | 12/2021 |
| WO | 2021252319 | 12/2021 |
| WO | 2021252320 | 12/2021 |
| WO | 2022217193 | 10/2022 |
| WO | 2022258572 | 12/2022 |

OTHER PUBLICATIONS

Lam, Carly Siu Yin, et al., "Defocus Incorporated Multiple Segments (DIMS) spectacle lenses slow myopia progression: a 2-year randomised clinical trial," Br. J. Ophthalmol. 0:1-6 (2019).

Torii, Hidemasa, et al., "Violet Light Exposure Can Be a Preventive Strategy Against Myopia Progression," EBioMedicine 15:210-219 (2017).

Adler, Daniel, et al., "The possible effect of under correction on myopic progression in children." Clin Exp Optom., 89:315-321 (2006).

Aleman, Andrea C., et al.,, "Reading and Myopia: Contrast Polarity Matters," Scientific Reports, 8 pages (2018).

Arden, G.B., et al., "Does dark adaptation exacerbate diabetic retinopathy? Evidence and a linking hypothesis," Vision Research 38:1723-1729 (1998).

Arden, GB, et al, "Regression of early diabetic macular edema is associated with prevention of dark adaptation", in Eye, (2011). 25, pp. 1546-1554.

Benavente-Perez, A., et al., "Axial Eye Growth and Refractive Error Development Can be Modified by Exposing the Peripheral Retina to Relative Myopic or Hyperopic Defocus," Invest Ophthalmol Vis Sci., 55:6765-6773 (2014).

Bonar, Jr, et al, "High brightness low power consumption microLED arrays", in SPIE DigitalLibrary.org/conference-proceedings-of-spie, SPIE OPTO, 2016, San Francisco, California, United States, Abstract Only.

Carr, Brittany J., et al., "The Science Behind Myopia," retrieved from https://webvision.med.utah.edu/book/part-xvii-refractive-errors/the-science-behind-myopia-by-brittany-j-carr-and-william-k-stell/, 89 pages (2018).

Chakraborty, R., et al., "Diurnal Variations in Axial Length, Choroidal Thickness, Intraocular Pressure, and Ocular Biometrics," IOVS, 52(8):5121-5129 (2011).

Chakraborty, R., et al., "Hyperopic Defocus and Diurnal Changes in Human Choroid and Axial Length," Optometry and Visual Science, 90(11):1187-1198 (2013).

Chakraborty, R., et al., "Monocular Myopic Defocus and Daily Changes in Axial Length and Choroidal Thickness of human Eyes," Exp Eye Res, 103:47-54 (2012).

Cooper, J., et al, "Current status of the development and treatment of myopia", Optometry, 83:179-199 (2012).

Cooper, J., et al., "A Review of Current Concepts of the Etiology and Treatment of Myopia," Eye & Contact Lens, 44(4):231-247 (Jul. 2018).

Demory, B., et al, "Integrated parabolic microlenses on micro LED color pixels", in Nanotechnology, (2018); 29, 16, pp. 1018, Abstract Only.

Dolgin, Elle, "The Myopia Boom," Nature 519:276-278 (2015).

Edrington, Timothy B., "A literature review: The impact of rotational stabilization methods on toric soft contact lens performance," Contact Lens & Anterior Eye, 34:104-110 (2011).

Flitcroft, D.I., "The complex interactions of retinal, optical and environmental factors in myopia aetiology," 31(6):622-660 (2012).

Garner, L.F., et al., "Crystalline Lens Power in Myopia," Optometry and Vision Science, 69:863-865 (1992).

Gwiazda, Jane, "Treatment Options for Myopia," retrieved from https://www.ncbi.nlm.nih.gov/pmc/articles/PMC2729053/, Optom Vis Sci., 86(6):624-628 (Jun. 2009).

Gwiazda, Jane, et al, "A Randomized Clinical Trial of Progressive Addition Lenses versus Single Vision Lenses on the Progression of Myopia in Children", Invest Ophthalmol Vis Scl, 44:1492-500 [PubMed: 12657584] (2003).

Hammond, D.S., et al, "Dynamics of active emmetropisation in young chicks—influence of sign and magnitude of imposed defocus" Ophthalmic Physiol Opt. 33:215-222 (2013).

Henry W., "MicroLED Sources enable diverse ultra-low power applications", in Photonic Spectra, 2013.

Jones, D., "Measure Axial Length to Guide Myopia Management," Review of Myopia Management, 5 pages (Apr. 9, 2020).

Kur, Joanna, et al., "Light adaptation does not prevent early retinal abnormalities in diabetic rats," Scientific Reports, 8 pages (Feb. 8, 2016).

Lagreze, Wolf A., et al., "Preventing Myopia," retrieved from https://www.ncbi.nlm.nih.gov/pmc/articles/PMC5615392/, Dtsch Arztebl Int., 114(35-36):575-580 (Sep. 2017).

Leo, Seo-Wei, et al., "An evidence-based update on myopia and interventions to retard its progression," J AAPOS, 15(2): 181-189 (Apr. 2011).

Lingley, A.R., et al, : A single pixel wireless contact lens display, in J Micromech. Microeng., 2011; 21, 125014; doi:10.1088/0960-1317/21/12/125014, Abstract Only.

Martin, J.A., et al., "Predicting and Assessing Visual Performance with Multizone Bifocal Contact Lenses," Optom Vis Sci, 80(12):812-819 (2003).

Matkovic, K., et al., "Global Contrast Factor—a New Approach to Image Contrast," Computational Aesthetics in Graphics, Visualization and Imaging, 9 pages (2005).

McKeague C, et al. "Low-level night-time light therapy for age-related macular degeneration (ALight): study protocol for a randomized controlled trial", in Trials 2014, 15:246, http://www.trialsjournal.com/content/15/1/246.

Moreno, I, "Creating a desired lighting pattern with an LED array" in Aug. 2008, Proceedings of SPIE—The International Society for Optical Engineering 7058, DOI: 10.1117/12.795673.

Moreno, I., "Modeling the radiation pattern of LEDS", in Optics Express, 2008; 16, 3 pp. 1808.

Nickla, Debora L., et al., "Brief hyperopic defocus or form deprivation have varying effects on eye growth and ocular rhythms depending on the time-of-day of exposure," Exp Eye Res. 161:132-142 (Aug. 2017).

Ramsey, DJ, and Arden, GB, "Hypoxia and dark adaptation in diabetic retinopathy: Interactions, consequences and therapy", in Microvascular Complications-Retinopathy (JK Sun, ed.), Cur Dab Rep (2015) 15: 118, DOI 10.1007/s11892-015-0686-2, Abstract Only.

Read, Scott A., et al., "Choroidal changes in human myopia: Insights from optical coherence tomography imaging," Clin Exp Optom, 16 pages (2018).

Read, Scott A., et al., "Human Optical Axial Length and Defocus," IOVS, 51(12):6262-6269 (2010).

Shivaprasad, S, et al, "Clinical efficacy and safety of a light mask for prevention of dark adaptation in treating and preventing progression of early diabetic macular oedema at 24 months (CLEOPATRA): a multicentre, phase 3, randomised controlled trial," in www.thelancet.com/diabetes-endocrinology vol. 6, pp. 382-391 ( May 2018).

Smith, III, Earl L., "Optical treatment strategies to slow myopia progression: Effects of the visual extent of the optical treatment zone," retrieved from https://www.ncbi.nlm.nih.gov/pmc/articles/PMC3624048/, Exp Eye Res., 114:77-88 (Sep. 2013).

Srinivasan, S., "Ocular axes and angles: Time for better understanding," J. Cataract Refract. Surg., 42:351-352 (Mar. 2016).

Wallman, Josh, et al., "Homeostasis of Eye Growth and the Question of Myopia," Neuron, 43:447-468 (2004).

Wolffsohn, James A., et al., "Impact of Soft Contact Lens Edge Design and Midperipheral Lens Shape on the Epithelium and Its Indentation With Lens Mobility," IOVS, 54(9):6190-6196 (2013).

Haglund, Erik, et al., "Multi-wavelength VCSEL arrays using high-contrast gratings," Proc. of SPIE vol. 10113, 7 pages (2017).

(56) References Cited

OTHER PUBLICATIONS

International Application No. PCT/US2021/036100, filed June 7, 2021 (86 pages).
International Patent Application No. PCT/US2021/032162, filed May 13, 2021 (58 pages).
International Patent Application No. PCT/US2021/036102, filed Jun. 7, 2021 (67 pages).
International Patent Application No. PCT/US2021/070166, filed Feb. 19, 2021 (79 pages).
Jayaraman, V., et al., "Recent Advances in MEMS-VCSELs for High Performance Structural and Functional SS-OCT Imaging," Proc. of SPIE vol. 8934, retrieved from http://proceedings.spiedigitallibrary.org/ on Dec. 1, 2015 (2014).
U.S. Appl. No. 17/304,666, filed Jun. 24, 2021 (67 pages).
U.S. Appl. No. 17/302,479, filed May 4, 2021 (60 pages).
U.S. Appl. No. 17/302,827, filed May 13, 2021 (52 pages).
U.S. Appl. No. 17/303,889, filed Jun. 9, 2021 (69 pages).
U.S. Appl. No. 17/304,630, filed Jun. 23, 2021 (68 pages).
U.S. Appl. No. 17/304,691, filed Jun. 24, 2021 (88 pages).
Brennan NA, Toubouti YM, Cheng X, Bullimore MA. Efficacy in myopia control. Prog Retin Eye Res. Jul. 2021; 83:100923. Epub Nov. 27, 2020.
Walline JJ, Lindsley K, Vedula SS, Cotter SA, Mutti DO, Twelker JD. Interventions to slow progression of myopia in children. Cochran Database Syst Rev. Dec. 7, 2011; (12):CD004916.
Zhou WJ, Zhang YY, Li H, Wu YF, Xu J, Lv S, Li G, Liu SC, Song SF. Five-year progression of refractive errors and incidence of myopia in school-aged children in western China. J Epidemiol. Jul. 5, 2016; 26(7):386-95. Epub Feb. 13, 2016.
"Design Considerations for Overmolding and Insert Molding," Proto Labs, retrieved May 6, 2024 from chrome-extension://efaidnbmnnnibpcajpcglclefindmkaj/https://vertassets.blob.core.windows.net/download/777c536d/777c536d-f935-4a3a-aa9e-bff37143c1dd/pl_designconsiderations_for_om_im_wp_final.pdf, applicant believes that the teachings of this reference was known prior to Apr. 6, 2021.
"What Is Insert Molding? Process, Considerations & Applications," retrieved May 6, 2024 from https://www.rapiddirect.com/blog/what-is-insert-molding/, applicant believes that the teachings of these reference was known prior to Apr. 6, 2021.

* cited by examiner

METHOD AND APPARATUS FOR TREATING REFRACTIVE ERROR OF THE EYE

CROSS REFERENCE

This application is a 371 national phase of PCT/US2019/030682, filed May 3, 2019, and claims the benefit under 35 U.S.C. § 119 (e) of United States Provisional Application No. 62/669,580, filed May 10, 2018, entitled "METHODS AND APPARATUSES OF TREATING REFRACTIVE ERROR OF THE EYE", the disclosures of which are incorporated, in their entirety, by this reference.

BACKGROUND

Prior approaches to vision correction of refractive error of the eye are less than ideal in at least some respects. Although spectacles and contact lenses can correct vision, these corrective devices may not decrease the onset and severity of myopia and other refractive errors. Similarly, most surgical approaches do not address the underlying causes of ocular development that can result in the eye having refractive error.

In light of the above, improved methods and apparatus of treating refractive error of the eye are needed. Ideally, such methods and apparatus would at least partially address the progression and onset of refractive error of the eye such as myopia.

SUMMARY

Embodiments of the present disclosure provide improved methods and apparatus for the treatment of refractive error with light, such as violet light. In some embodiments, a source of light energy such as a source of violet light energy is coupled to a structure configured to contact the eye. The light source and structure are arranged to provide therapeutic amounts of light such as violet light energy to the eye in order to inhibit the progression or onset of refractive error such as myopia. The light source can be configured in many ways and may comprise a radioisotope and a phosphorescent material. The structure configured to contact the eye may comprise a contact lens or an implant.

In a first aspect, an apparatus to treat refractive error of an eye comprises a structure to contact the eye, and a light source coupled to the structure. The light source is configured to direct light energy toward a retina of the eye to treat the refractive error of the eye.

In some embodiments, the light source emits violet light.

In some embodiments, the structure comprises a contact lens, and optionally the light source is one or more of embedded in the contact lens, located on an anterior surface of the contact lens, or located on a posterior surface of the contact lens.

In some embodiments, the light energy comprises violet light energy comprising a wavelength within a range from about 360 nm to about 400 nm.

In some embodiments, the light energy comprises violet light energy and the light source is configured to direct the violet light energy to the retina with an irradiance within a range from about 0.1 mW/cm2 to 5 mW/cm2.

In some embodiments, the light source illuminates a pupil of the eye with light energy in the range 0.1 nit to 10 nits and optionally within the range from 0.5 nits to 10 nits.

In some embodiments, the contact lens comprises one or more of a structure anterior to the light source to reflect light to the retina of the eye, a structure posterior to the light source to focus light onto the retina of the eye, a lens structure posterior to the light source to focus light onto the retina of the eye, or a diffractive structure posterior to the light source to diffract light toward the retina of the eye.

In some embodiments, the contact lens comprises a lens body, the lens body comprising one or more of a soft contact lens, a hydrogel contact lens, a hard contact lens, a rigid gas permeable contact lens, a polymethyl methacrylate contact lens, or an orthokeratology contact lens.

In some embodiments, the light energy comprises light energy violet light energy and the contact lens is configured to direct the violet light energy onto a cornea and toward the retina with an amount sufficient to promote a curvature change to the cornea of the eye.

In some embodiments, the structure comprises a contact lens comprising a posterior surface comprising a posterior radius of curvature sized to fit a cornea of the eye, and an anterior surface comprising an anterior radius of curvature configured to correct vision of the eye, and optionally the anterior surface comprises a second anterior radius of curvature oriented in relation to the anterior radius of curvature to correct an astigmatism of the eye.

In some embodiments, the structure to contact the eye comprises an implantable structure and the implantable structure comprises a covering disposed over the light source, and optionally the implant is configured to be turned on and off by a person who received the implant.

In some embodiments, the light source comprises one or more of a radioluminescent light source, a light emitting diode, a laser diode, a radioactive material, or a phosphorescent material, and optionally the radioactive material comprises tritium or radium.

In some embodiments, the structure to contact the eye comprises an optically transmissive material comprising a transmittance of at least 40% at 360 nm.

In some embodiments, the light source is arranged in a pattern on the structure to contact the eye, the pattern comprising one or more of: a spatial pattern on the structure to contact the eye, a spatial pattern located on an optically used portion of a contact lens, a spatial pattern on an inner portion of the contact lens to transmit light to the retina when the pupil constricts, a circular pattern, or a radial pattern, and optionally the structure to contact the eye comprises a contact lens.

In some embodiments, the apparatus comprises a contact lens comprising a posterior surface shaped to receive a cornea of the eye, a contact lens material comprising an index of refraction configured to transmit violet light from the source toward the retina, the contact lens comprising an anterior surface shaped to correct a refractive error of the eye in combination with the index of refraction and the posterior surface, and optionally the contact lens is configured to correct higher order aberrations comprising optical aberrations above third order, and optionally the contact lens comprises a multifocal contact lens configured to correct presbyopia.

In another aspect, a method comprises treating an eye with the apparatus of any one of the preceding claims.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1B:
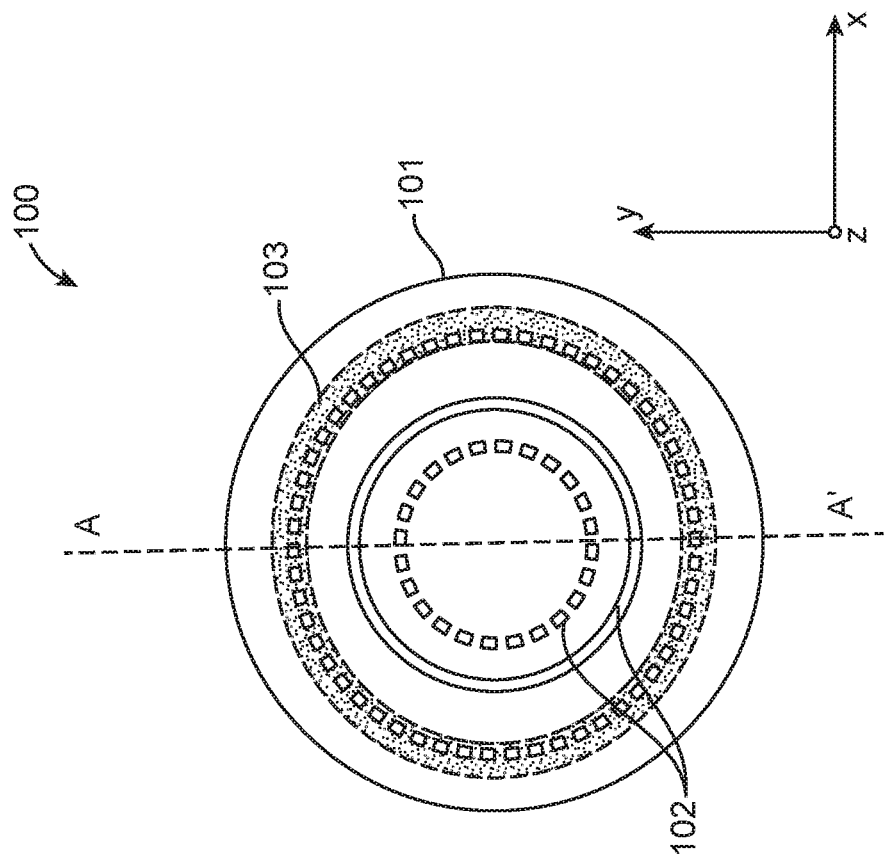
FIG. 1B shows a front view of the contact lens of FIG. 1A.

The methods and apparatus disclosed herein are well suited for combination with prior approaches to vision correction. For example, the structure to contact the eye may comprise a contact lens or an implant. Such structure may function normally to correct refractive errors and focus light into the eye, while the light source coupled to the structure may emit light such as violet light toward a retina of the eye to treat the refractive error of the eye. In some embodiments, such emission of violet light and violet light received by the eye may be controlled at a level so that there may not be noticeable influence on the functions of the eye.

In some embodiments, the apparatuses and methods disclosed herein are configured to prevent progression or onset of refractive errors in the eye(s). In some embodiments, the apparatuses and methods disclosed herein are configured to treat or improve refractive conditions in the eye(s). In some embodiments, the apparatuses and methods herein promote a curvature change to the cornea of the eye thereby improving refractive conditions in the eye(s), for example with orthokeratology assisted by light such as violet light. In some embodiments, the apparatuses and methods herein inhibit inappropriate increases or allow controlled amounts of increase to the axial length of the eye thereby reducing refractive errors in the eye(s) such as myopia.

In some embodiments, an apparatus to treat refractive error of an eye comprises: a structure to contact the eye; a light source coupled to the structure; wherein the light source is configured to emit violet light energy toward a retina of the eye to treat the refractive error of the eye. In some embodiments, the structure comprises a contact lens. The light source can be embedded in the contact lens, on an anterior surface of the contact lens, or on a posterior surface of the contact lens and combinations thereof. In some embodiments, the violet light comprises a wavelength within a range from about 360 nm to about 400 nm. In some embodiments, the light source is configured to direct violet light energy to the retina with a luminance is less than 5 mW/cm$^2$. In some embodiments, the light source illuminates the pupil of the eye with light energy in the range from 0.1 nit to 10 nit (candelas per square meter), preferably from 0.5 nit to 2 nits. In some embodiments, the contact lens comprises a structure anterior to the light source to reflect light to the retina of the eye, a structure posterior to the light source to focus light onto the retina of the eye, a lens structure posterior to the light source to focus light onto the retina of the eye, or a diffractive structure posterior to the light source to diffract light toward the retina of the eye, and combinations thereof. In some embodiments, the contact lens comprises a lens body, in which the lens body comprises a soft contact lens, a hydrogel contact lens, a hard contact lens, a rigid gas permeable contact lens, a polymethyl methacrylate contact lens, or an orthokeratology contact lens, and combinations thereof. In some embodiments, the contact lens is configured to direct the violet light energy onto a cornea and toward the retina with an amount sufficient to promote a curvature change to the cornea of the eye. In some embodiments, the structure comprises a contact lens comprising a posterior surface comprising a posterior radius of curvature sized to fit a cornea of the eye, and an anterior surface comprising an anterior radius of curvature configured to correct vision of the eye. In some embodiments, the anterior surface comprises a second anterior radius of curvature oriented in relation to the anterior radius of curvature to correct an astigmatism of the eye.

In some embodiments, the structure to contact the eye comprises an implantable structure, in which the implantable structure comprises a covering disposed over the light source. The implant can be configured to be turned on and off by a person who received the implant.

The light source can be configured in many ways. In some embodiments, the light source comprises a radioluminescent light source, a light emitting diode, a laser diode, a radioactive material, or a phosphorescent material and combinations thereof. The radioactive material may comprise tritium or radium, for example.

In some embodiments, the structure to contact the eye comprises an optically transmissive material comprising a transmittance of at least 40% at 360 nm.

In some embodiments, the light source is arranged in a spatial pattern on the structure to contact the eye. The spatial pattern can be located on an optically used portion of a contact lens, on an inner portion of the contact lens to transmit light to the retina when the pupil constricts, or in a circular pattern or a radial pattern on the contact lens, and combinations thereof.

In some embodiments, the apparatus comprises a contact lens comprising a posterior surface shaped to receive a cornea of the eye, a contact lens material comprising an index of refraction and configured to transmit violet light from the source toward the retina, an anterior surface shaped to correct a refractive error of the eye in combination with the index of refraction and the posterior surface. In some embodiments, the contact lens is configured to correct higher order aberrations comprising optical aberrations above third order, and the contact lens may comprise a multifocal contact lens configured to correct presbyopia.

In some embodiments, a method of treating the eye comprises treating an eye with the apparatus(es) as disclosed herein, such as a contact lens or an implant as disclosed herein.

Figure 1A:
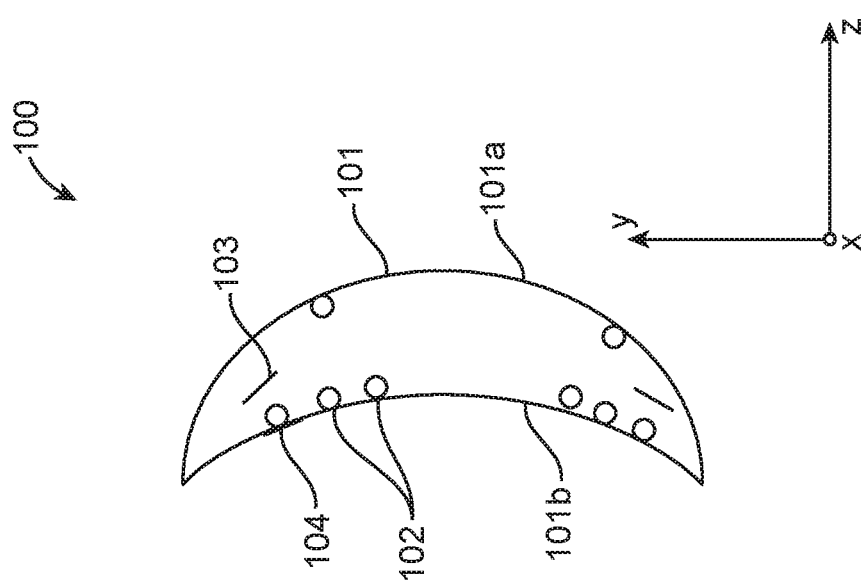
FIG. 1A shows a contact lens configured to treat refractive error of the eye in a cross-sectional view, in accordance with some embodiments.

Referring to FIGS. 1A to 1B, in accordance with some embodiments, the apparatus 100 comprises a structure to contact the eye 101. In some embodiments, the structure 101 comprises a contact lens or an intraocular lens (IOL). In some embodiments, the contact lens 101 includes a lens body. Nonlimiting examples of the lens body include a soft contact lens, a hydrogel contact lens, a hard contact lens, a rigid gas permeable contact lens, a polymethyl methacrylate contact lens, or an orthokeratology contact lens, and combinations thereof. In some embodiments, the contact lens has a posterior surface 101b comprising a posterior radius of curvature sized to fit a cornea of the eye, and an anterior surface 101a comprising an anterior radius of curvature configured to correct vision of the eye. In some embodiments, the anterior surface also includes a second anterior radius of curvature oriented in relation to the anterior radius of curvature to correct astigmatism of the eye. In some embodiments, the contact lens material has an index of refraction and is configured to focus violet light from the source toward the retina. In some embodiments, the anterior surface 101a is shaped to correct a refractive error of the eye (e.g., myopia, hyperopia, presbyopia, and astigmatism) with a combination of the index of refraction and the posterior surface 101b. In some embodiments, the contact lens is configured to correct higher order aberrations comprising optical aberrations of third order, e.g. coma, and above, e.g. spherical aberration. In some embodiments, the contact lens comprises a multifocal contact lens configured to correct presbyopia.

In some embodiments, the contact lens material has an index of refraction and is configured to transmit violet light from the source toward the retina. In some embodiments, the structure to contact the eye 101 has an optically transmissive material comprising a transmittance of at least 30%, 40%, 50%, or 60% at one or more of 350 nm, 360 nm, 370 nm, 380 nm, 390 nm, or 400 nm. In some embodiments, the transmittance is at least 30%, 40%, 50%, or 60% in the entire range from 350 nm to 400 nm.

In some embodiments, the apparatus 100 includes the light source 102 that is coupled to the structure 101. The light source 102 may comprise a plurality of light sources. In some embodiments, the light source is embedded in the structure, and the light source may be embedded in one or more locations of the structure. Such locations may include the optically used portion of the lens. For example, the light source can be located anywhere on an anterior surface 101a of the contact lens 101, or on a posterior surface 101b of the contact lens and combinations thereof. In some embodiments, the light source may be spatially distributed in various patterns. In some embodiments, the spatial pattern may be located on an optically used portion of a contact lens, on an inner portion of the contact lens, or both, to transmit light to the retina (e.g., when the pupil constricts). In some embodiments, the light source may be distributed or in a circular pattern or a radial pattern on the contact lens, and combinations thereof. As shown in FIG. 1B, the light source may be distributed in multiple concentric rings with fixed or variable gaps therebetween. In some embodiments, the light source may be distributed in a donut pattern. Nonlimiting examples of patterns in which the light source may be spatially distributed include: a web-like pattern, a spiral pattern, a swirl pattern, and a radially scatter pattern (optionally from the center of the structure). In some embodiments, the spatial pattern may include areas that are at or substantially at the circumference of the structure (e.g., less than 3 mm, 2 mm, 1 mm, 0.5 mm, 0.2 mm or less to the circumference). As an example, the light source includes multiple concentric rings with a largest ring covering the entire circumference.

In some embodiments, the light source is configured to emit optical energy toward a retina of the eye to treat the refractive error of the eye. As shown in FIGS. 1A and 1B, the light source emits violet light toward the eye. FIG. 1A shows the cross section at A-A' in FIG. 1B. The violet light may comprise a wavelength within a range from about 350 nm to about 400 nm. In some embodiments, the light source is configured to direct violet light energy to the retina with a radiance less than 5 mW/cm$^2$. The radiance of the violet light can be within a range from about 0.01 mW/cm$^2$ to about 5 mW/cm$^2$, for example. Continuing to refer to FIGS. 1A-1B, in some embodiments, the contact lens 101 has a structure 103 anterior to the light source to reflect light to the retina of the eye. Alternatively or in combination, a structure 104 can be located posterior to the light source 102 in order to focus light onto the retina of the eye. The structure 104 may comprise a lens structure posterior to the light source to focus light onto the retina of the eye, or a diffractive structure posterior to the light source to diffract light toward the retina of the eye, and combinations thereof. Alternatively or in combination, the light source can be located closer to the posterior surface of the lens than the anterior surface in order to decrease absorbance of the contact lens material.

In some embodiments, the structure to contact the eye 101 comprises an implantable structure which may comprise a covering disposed over the light source and optionally wherein the implant is configured to be turned on and off, for example, by a person who received the implant or by a trigger external to the implant such as intensity of ambient light detected by the implant.

In some embodiments, the contact lens 101 or the implant is configured to direct the violet light energy onto a cornea and toward the retina with an amount sufficient to promote a curvature change to the cornea of the eye. In some embodiments, the light source is configured to emit the light at a substantially constant level (e.g. within 25%) for a pre-determined period of time, e.g., for at least 12 hours, 1 day, 1 week, 2 weeks, 1 month, or even longer. In some embodiments, the light source is configured to emit the light when triggered by an external trigger. Non-limiting exemplary triggers may include ambient light, opening or closing of the eyelid, a temperature at the light source, etc. In some embodiments, the light source is configured to remain substantially fixed in its spatial location relative to the eye of the patient.

In some embodiments, the light source 102 is configured to direct violet light energy to the retina with a luminance. The light source may have a radioluminescent light source, a light emitting diode, a laser diode, a radioactive material, a phosphorescent material, or a chemiluminescent compound, and combinations thereof. In some embodiments, the radioactive material includes tritium and/or radium.

In some embodiments, the irradiance (energy per unit area) of the violet light (e.g., having a wavelength within the range of 350 nm to 400 nm) emitted from the light source and/or that reaches the eye is not particularly limited. In some embodiments, the irradiance is preferably determined by taking into consideration the effect of the on the human eye and skin, and the duration of the exposure. When light is emitted toward the eye for a long period of time for the purpose of myopia prevention, the irradiance relates to the light emission time as well, and may be increased if the time is short, but is preferably decreased if the time is long. In some embodiments, the irradiance may be 20.0 mW/cm$^2$ or less. In some embodiments, the irradiance may be 10.0 mW/cm$^2$ or less. In some embodiments, the irradiance may be 80.0 mW/cm$^2$ or less. In some embodiments, the irradiance may be 5.0 mW/cm$^2$ or less. In some embodiments, the preferred irradiance is 3.0 mW/cm$^2$ or less. In some embodiments, the irradiance is preferably 2.0 mW/cm$^2$ or less, and is preferably decreased to 1.0 mW/cm$^2$, 0.5 mW/cm$^2$ or less, 0.1 mW/cm$^2$ or less, or 0.05 mW/cm$^2$ or less as the time increases. The irradiance may comprise an amount within a range defined by any two of the preceding values. The irradiance can be measured using a known method. It should be noted that "irradiance" indicates the intensity or energy of the light that enters or reaches the eye.

In some embodiments, the structure to contact the eye includes apiece of eyewear such as an eyeglass, or a goggle.

The presently disclosed methods and apparatus are well suited for combination with many types of lenses, such as one or more of: smart contact lenses, contact lenses with antennas and sensors, contact lenses with integrated pulse oximeters, contact lenses with phase map displays, electro-optic contact lenses, contact lenses with flexible conductors, autonomous eye tracking contact lenses, electrochromic contact lenses, dynamic diffractive liquid crystal lenses, automatic accommodation lenses, image display lenses with programmable phase maps, lenses with tear activated micro batteries, tear film sensing contact lenses, lenses with multi-colored LED arrays, contact lenses with capacitive sensing, lenses to detect overlap of an ophthalmic device by an eyelid, lenses with active accommodation, lenses with electrochemical sensors, lenses with enzymes and sensors, lenses including dynamic visual field modulation, lenses for measuring pyruvate, lenses for measuring urea, lenses for measuring glucose, lenses with tear fluid conductivity sensors, lenses with near eye displays with phase maps, or lenses with electrochemical sensor chips.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An apparatus to treat refractive error of an eye, comprising:
   a first structure configured to contact an anterior surface of the eye, the first structure comprising a refractive lens shaped to correct a refractive error of the eye;
   a light source coupled to the first structure;
   a second structure on the first structure to focus a light energy from the light source toward a retina of the eye and comprising a refractive, diffractive, or reflective structure; and
   a third structure to direct light to the retina of the eye, the third structure configured to be located more anterior to the anterior surface of the eye than the light source and comprising a reflective structure;
   wherein the light source and the second structure are configured to concentrate the light energy on the retina of the eye with an irradiance on the retina within a range from 0.1 mW/cm$^2$ to 5 mW/cm$^2$ to treat the refractive error of the eye.

2. The apparatus of claim 1, wherein the light source emits violet light.

3. The apparatus of claim 1, wherein the first structure comprises a contact lens.

4. The apparatus of claim 3, wherein the contact lens comprises a lens body, the lens body comprising one or more of a soft contact lens, a hydrogel contact lens, a hard contact lens, a rigid gas permeable contact lens, a polymethyl methacrylate contact lens, or an orthokeratology contact lens.

5. The apparatus of claim 3, wherein the light energy comprises violet light energy and the contact lens is configured to direct the violet light energy onto a cornea and toward the retina with an amount sufficient to promote a curvature change to the cornea of the eye.

6. The apparatus of claim 1, wherein the light energy comprises violet light energy comprising a wavelength within a range from 360 nm to 400 nm.

7. The apparatus of claim 1, wherein the light energy comprises violet light energy and the light source is configured to direct the violet light energy to the retina.

8. The apparatus of claim 1, wherein the light source illuminates a pupil of the eye with the light energy in a range from 0.1 nit to 10 nits.

9. The apparatus of claim 1, wherein the first structure comprises a contact lens comprising a posterior surface comprising a posterior radius of curvature sized to fit a cornea of the eye, and an anterior surface comprising an anterior radius of curvature configured to correct vision of the eye.

10. The apparatus of claim 1, wherein the structure to contact the eye comprises an implantable structure and wherein the implantable structure comprises a covering disposed over the light source.

11. The apparatus of claim 1, wherein the light source comprises one or more of a radioluminescent light source, a light emitting diode, a laser diode, a radioactive material, or a phosphorescent material.

12. The apparatus of claim 1, wherein the structure to contact the eye comprises an optically transmissive material comprising a transmittance of at least 40% at 360 nm.

13. The apparatus of claim 1, wherein the light source is arranged in a pattern on the structure to contact the eye, the pattern comprising one or more of: a spatial pattern on the structure to contact the eye, a spatial pattern located on an optically used portion of a contact lens, a spatial pattern on an inner portion of the contact lens to transmit light to the retina when a pupil constricts, a circular pattern, or a radial pattern.

14. The apparatus of claim 1, wherein the apparatus comprises a contact lens comprising a posterior surface shaped to receive a cornea of the eye, a contact lens material comprising an index of refraction configured to transmit violet light from the source toward the retina, the contact lens comprising an anterior surface shaped to correct a refractive error of the eye in combination with the index of refraction and the posterior surface.

15. A method, the method comprising treating an eye with the apparatus of claim 1.

* * * * *